(12) United States Patent
Chen

(10) Patent No.: US 10,342,713 B2
(45) Date of Patent: Jul. 9, 2019

(54) WETNESS NOTIFICATION SYSTEM FOR DETECTING AND NOTIFYING WETNESS IN CLOTHING ARTICLE

(71) Applicant: Hung Chi Chen, Kaohsiung (TW)

(72) Inventor: Hung Chi Chen, Kaohsiung (TW)

(*) Notice: Subject to any disclaimer, the term of this patent is extended or adjusted under 35 U.S.C. 154(b) by 0 days.

(21) Appl. No.: 15/889,121

(22) Filed: Feb. 5, 2018

(65) Prior Publication Data

US 2018/0235818 A1     Aug. 23, 2018

(30) Foreign Application Priority Data

Feb. 17, 2017   (TW) .............................. 106202295 U

(51) Int. Cl.
| | | |
|---|---|---|
| A61F 13/42 | (2006.01) | |
| H04N 1/00 | (2006.01) | |
| H04N 5/225 | (2006.01) | |
| H04N 5/232 | (2006.01) | |

(52) U.S. Cl.
CPC ......... *A61F 13/42* (2013.01); *H04N 1/00106* (2013.01); *H04N 5/2256* (2013.01); *H04N 5/2257* (2013.01); *H04N 5/23293* (2013.01); *A61F 2013/424* (2013.01); *H04N 5/23203* (2013.01)

(58) Field of Classification Search
CPC ........................... A61F 13/42; A61F 2013/424

USPC .......................................................... 348/160
See application file for complete search history.

(56) References Cited

U.S. PATENT DOCUMENTS

2014/0198203 A1*  7/2014  Vardi ..................... G08B 21/20
                                                   348/135

* cited by examiner

*Primary Examiner* — Jeffery A Williams
(74) *Attorney, Agent, or Firm* — Pro-TECHTOR International Services; Ian Oglesby

(57) ABSTRACT

A wetness notification system includes a sampling unit (5) for contacting and sampling liquid within a space surrounded by a clothing article (10), a moisture detector (3) mounted in the clothing article (10) and outputting a notification signal, a processor module (6) for transceiving the notification signal, a camera device (9) and a user device (4). The camera device (9) includes a camera (90) facing the sampling unit (5) for capturing an image thereof, and a camera transceiver (902) for transceiving the image. The user device (4) includes a display (47), a device transceiver (41) communicating wirelessly with the processor module (6) and the camera transceiver (902) for receiving the notification signal and the image respectively therefrom, and a device processor (42) electrically connected to the device transceiver (41), and timing a time duration upon receiving the notification signal to output a control signal after the time duration has elapsed to enable the the camera (90) to capture the image, and controlling the display (47) to display the image.

14 Claims, 5 Drawing Sheets

WETNESS NOTIFICATION SYSTEM FOR DETECTING AND NOTIFYING WETNESS IN CLOTHING ARTICLE

FIELD

This disclosure relates to a notification system, more particularly to a wetness notification system with a camera device for detecting and notifying wetness in a clothing article.

BACKGROUND

A conventional diaper with a wetness sensing device includes a first non-woven fabric layer, two strip electrodes, a second non-woven fabric layer, a liquid absorbing layer made from a liquid absorbing material, a liquid-proof layer and two metallic sockets. A first side of the first non-woven fabric layer absorbs liquid excreted from a human body, and the liquid permeates to a second side of the first non-woven fabric layer. The strip electrodes are attached onto the second side of the first non-woven fabric layer, and the strip electrodes are electrically connected when they come into contact with the liquid. A first side of the second non-woven fabric layer is attached to the second side of the first non-woven fabric layer and to the strip electrodes, and the strip electrodes are thus retained between the first and second non-woven fabric layers. The first side of the second non-woven fabric layer absorbs the liquid, which permeates to a second side of the second non-woven fabric layer. The liquid absorbing layer is attached to the second side of the second non-woven fabric layer, and absorbs the liquid permeated through the second non-woven fabric layer. The liquid-proof layer is made from a liquid-proof material (i.e., a material that is impervious to liquids). A first side of the liquid-proof layer is attached to the second side of the liquid absorbing layer, and retains the liquid that has permeated through the liquid absorbing layer to prevent the liquid from leaking out of the diaper. Each of the metallic sockets has a first engaging portion that engages with a respective one of two engaging bodies of an electrical detection device. This enables the electrical detection device to detect the electrical conduction between the strip electrodes when a liquid is excreted, and to send a wetness notification signal for notifying a caregiver to change the diaper according to the wetness notification signal.

However, the electrical detection device requires a battery for operation. Due to the absence of a low electricity notification mechanism for notification when the battery is low in electricity, untimely changing of the diaper may lead to skin irritation, rashes or other skin diseases/conditions. Moreover, the strip electrodes are sewn into the diaper, and sewing increases labor costs and may cause a rise in the number of defective products.

A conventional wetness notification system disclosed in Taiwanese Patent Application Publication No. 201634018 for detecting wetness in a clothing article configured for absorbing urine not only solves the problems mentioned above, but further provides features such as urine sampling and urinalysis, for early diagnosis for certain diseases. For example, by sampling urine of a wearer of the clothing article and analyzing the concentrations of the substances therein, such as proteins, nitrite, glucose, ketones, bilirubin, occult blood, leukocytes, urobilinogen, etc., or analyzing the physical or chemical properties of the sampled urine, such as specific gravity, pH value, etc., a more thorough understanding of the user's health status can be obtained. However, the caregiver cannot become aware of the status of the diaper and information obtained by such conventional system when the caregiver is not nearby a wearer of the diaper equipped with such conventional wetness notification system.

SUMMARY

Therefore, an object of the disclosure is to provide a wetness notification system that can alleviate at least one of the drawbacks of the prior art.

According to one aspect of this disclosure, a wetness notification system is provided for detecting and notifying wetness in a clothing article configured for absorbing liquid. The wetness notification system includes a mounting module, a sampling unit, a moisture detector, a processing module, a camera device and a user device. The mounting module is configured to be disposed in the clothing article and defines an accommodating space. The sampling unit extends into the accommodating space, includes a substrate made of a flexible material and removably inserted into the accommodating space of the mounting module, and at least one sampling element disposed on the substrate for contacting and sampling liquid within a space surrounded by the clothing article for analysis. The moisture detector is mounted in the accommodating space, is positioned between the mounting module and the sampling unit, and is configured to output a notification signal when a surrounding moisture level detected thereby is greater than a threshold moisture level. The sampling element is disposed on a surface of the substrate that faces away from the moisture detector.

The processing module includes a casing, a wireless transmitter and a processing unit. The casing is mounted to the mounting module. The wireless transmitter is disposed in the casing. The processing unit is disposed in the casing, is electrically connected to the moisture detector and the wireless transmitter, and is configured to receive the notification signal outputted by the moisture detector and to transmit the notification signal through the wireless transmitter. The camera device is mounted to the mounting module and includes a camera, at least one securing component and at least one connecting component. The camera includes a camera module facing the sampling element for capturing an image of the sampling element, a camera transceiver, and a camera processor electrically connected to the camera module and the camera transceiver and configured to receive the image captured by the camera module and to process and wirelessly transmit the image through the camera transceiver. The securing component is secured to the mounting module. The connecting component interconnects the securing component and the camera. The user device includes a device transceiver, a display and a device processor. The device transceiver is configured to communicate wirelessly with the wireless transmitter and the camera transceiver for receiving the notification signal and the image respectively therefrom. The device processor is electrically connected to the device transceiver and the display, and is configured to start measuring a predetermined time duration upon receiving the notification signal from the device transceiver, to output a control signal to the camera processor through the device transceiver after the predetermined time duration has elapsed to enable the camera module to capture an image of the sampling element, and to control the display to display the image in response to receipt of the image from the camera through the device transceiver.

BRIEF DESCRIPTION OF THE DRAWINGS

Other features and advantages of the present disclosure will become apparent in the following detailed description of the embodiments of the disclosure, with reference to the accompanying drawings, in which.

DETAILED DESCRIPTION

Figure 1:
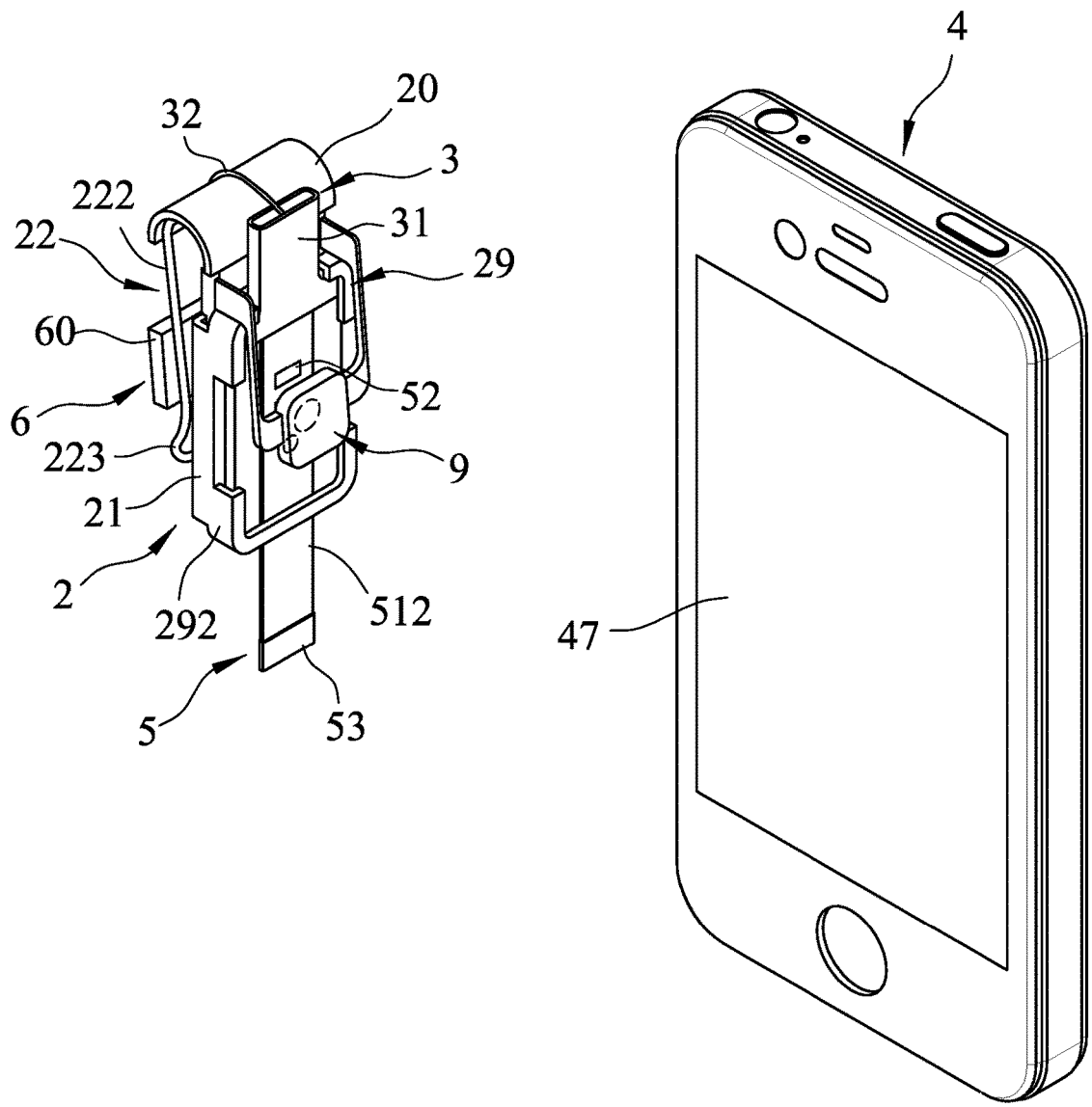
FIG. 1 is a schematic perspective view of a wetness notification system according to one embodiment of the present disclosure.
Figure 2:
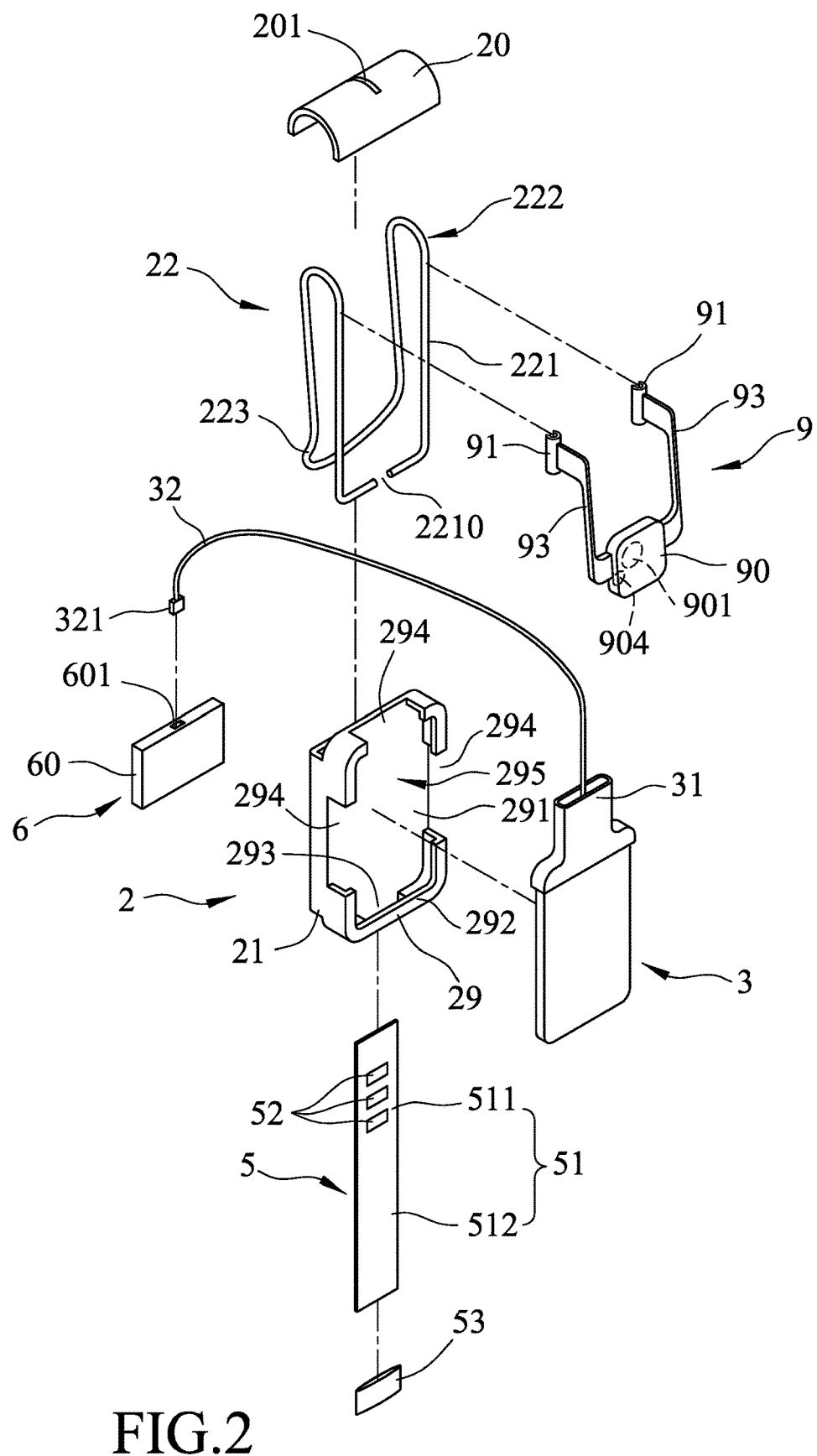
FIG. 2 is an exploded perspective view of part of the wetness notification system shown in FIG. 1.
Figure 3:
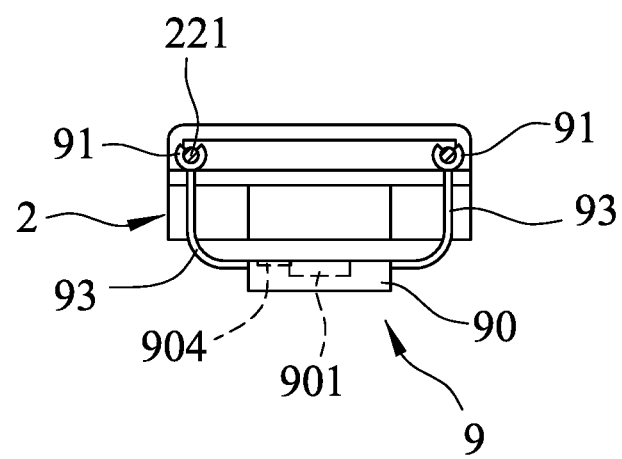
FIG. 3 is a schematic top view of part of the wetness notification system shown in FIG. 1.

Referring to FIGS. 1 to 3, one embodiment of the wetness notification system for detecting and notifying wetness in a clothing article 10 (see FIG. 5) that is for absorbing liquid according to the present disclosure is disclosed. For example, the clothing article 10 may be a pad-type diaper or a pant-type diaper and the liquid may be urine. The wetness notification system includes a mounting module 2, a moisture detector 3, a sampling unit 5, a processing module 6, a camera device 9 and a user device 4.

The mounting module 2 is mounted to the clothing article 10, and includes a positioning member 20, a clip unit 22, a sleeve body 21 and a mounting seat 29. The mounting seat 29 is combined with the sleeve body 21, and includes a base plate 291 and a positioning wall 292. The base plate 291 is connected to the sleeve body 21. The positioning wall 292 surrounds a periphery of the base plate 291, cooperates with the base plate 291 to define an accommodating space 295, and is formed with a through hole 293 and a plurality of notches 294 that are depressed toward the base plate 291.

The clip unit 22 includes a first portion 221 removably and partially inserted into the sleeve body 21, a second portion 222 curvedly extending from the first portion 221, and a third portion 223 extending from the second portion 222. In this embodiment, the first portion 221 has two separate segments defining a gap 2210 therebetween which facilitates deformation of the first portion 221 when the first portion 221 is being inserted into the sleeve body 21. The third portion 223 is configured to cooperate with the first portion 221 to clip the mounting module 2 onto the clothing article 10 in a manner that the sleeve body 21 and the mounting seat 29 are disposed at an inner side of the clothing article 10 and that the third portion 223 is disposed at an outer side of the clothing article 10 opposite to the inner side (see FIG. 5).

The moisture detector 3 is mounted in the accommodating space 295 for detecting a surrounding moisture level (i.e., the moisture level in a space surrounded by the clothing article 10), and is configured to output a notification signal when the surrounding moisture level detected thereby is greater than a threshold moisture level. The moisture detector 3 includes a connecting portion 31 extending through one of the notches 294, and a transmission wire 32 electrically between the connecting portion 31 and the processing module 6.

Figure 5:
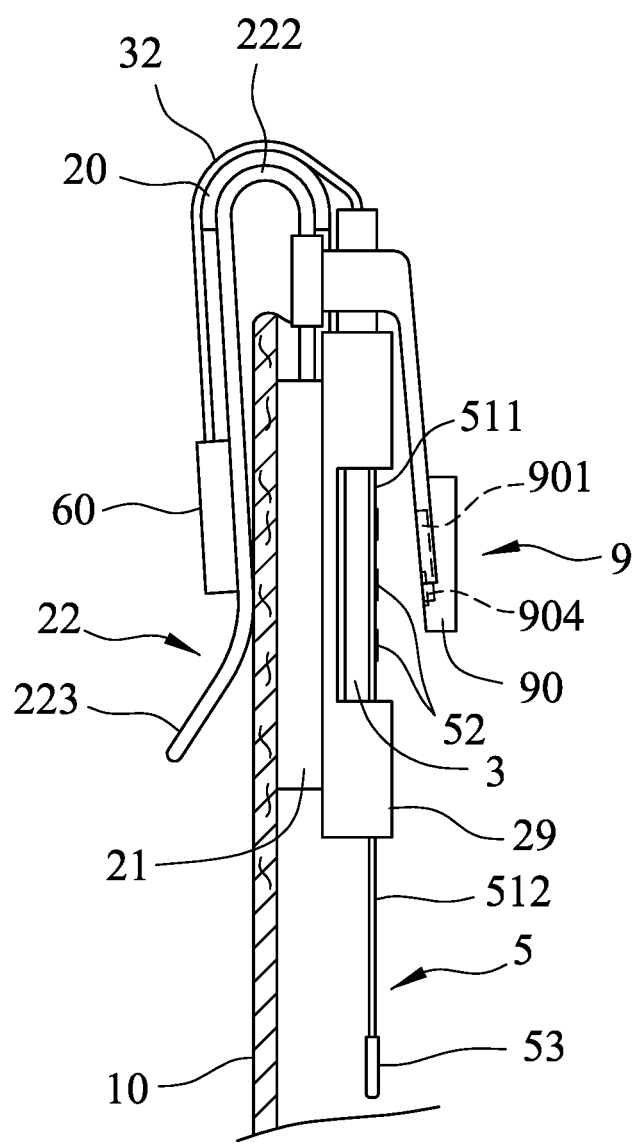
FIG. 5 is a fragmentary partly sectional view for illustrating the wetness notification system mounted to a clothing article.

The positioning member 20 engages the clip unit 22, and is formed with a slit 201 for receiving a section of the transmission wire 32 so as to position the transmission wire 32 as illustrated in FIG. 5.

The sampling unit 5 extends into the accommodating space 295, and includes a substrate 51 and a plurality of sampling elements 52 (for example, three sampling elements 52 in this embodiment). The substrate 51 is made of a flexible material and is removably inserted into the accommodating space 295 of the mounting module 2. The sampling elements 52 are disposed on a surface of the substrate 51 that faces away from the moisture detector 3, and are spaced apart from one another for contacting and sampling liquid within the space surrounded by the clothing article 10 for analysis. Each sampling element 52 may be a test paper for simultaneously sampling and testing the liquid as in this embodiment, or a vessel for sampling the liquid which is to be used for subsequent analysis in other embodiments of this disclosure. In should be noted that the number of the sampling elements 52 is not limited to three, and the sampling unit 5 may have one, two or more than three sampling elements 52 in other embodiments. The substrate 51 includes a first segment 511 disposed in the accommodating space 295 and mounted with the sampling elements 52, and a second segment 512 extending from the first segment 511 through the through hole 293 formed in the positioning wall 292 out of the mounting seat 29. The first segment 511 of the substrate 51 cooperates with the base plate 291 of the mounting seat 29 to sandwich the moisture detector 3 therebetwen, so that the moisture detector 3 is positioned between the base plate 291 and the first segment 511 and is tightly disposed in the accommodating space 295. In one embodiment, the sampling unit 5 further includes a protection sleeve 53 that is made of silicone, that covers a distal end of the second segment 512, and that has a curved end opposite to the first segment 511 for reducing discomfort of a wearer who wears the clothing article 10 when the wearer is in direct contact with the protection sleeve 53.

Figure 4:
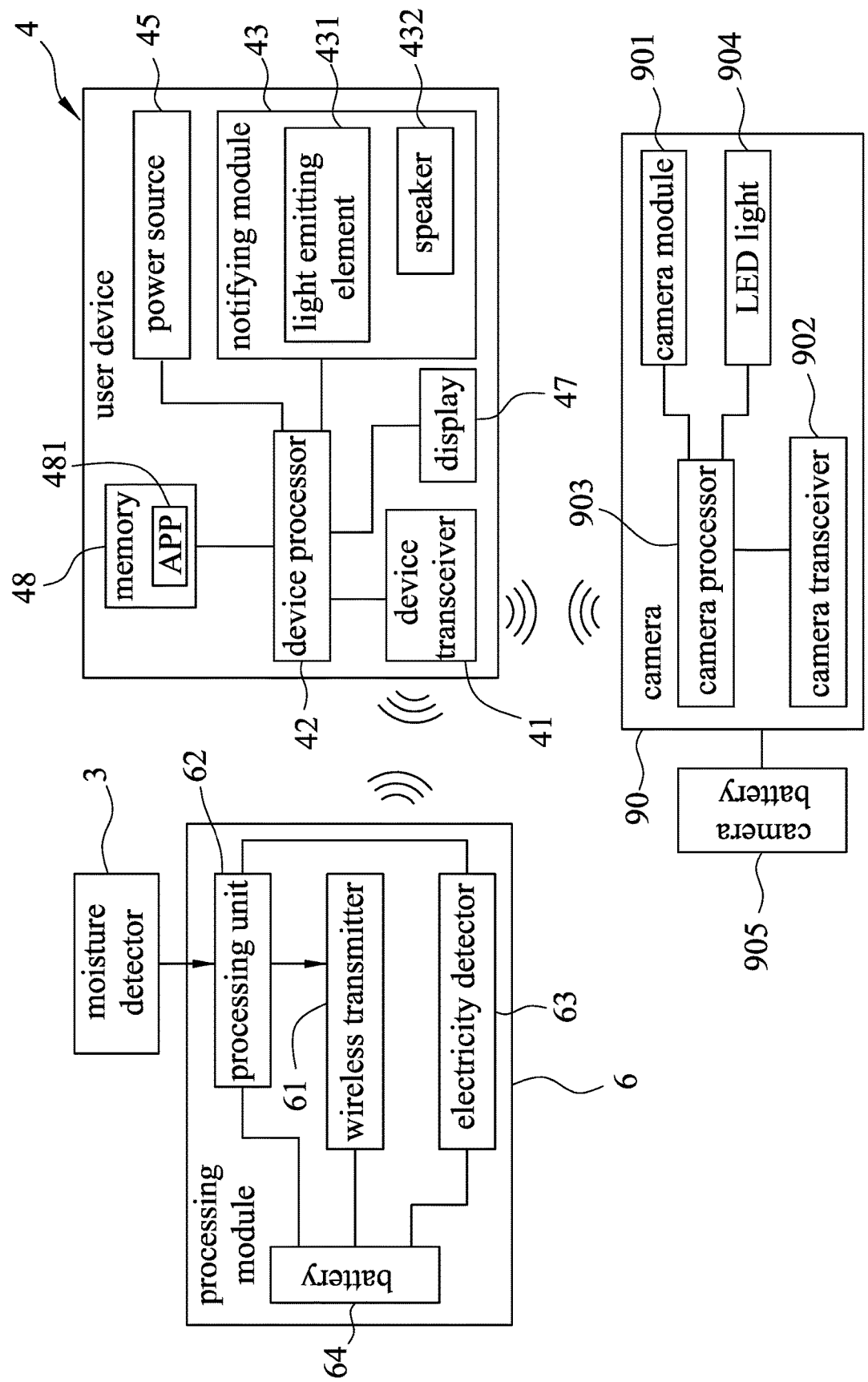
FIG. 4 is a block diagram of a moisture detector, a user device and a camera device of the wetness notification system according to one embodiment of the present disclosure.

Further referring to FIGS. 4 and 5, the processing module 6 includes a casing 60, a wireless transmitter 61 and a processing unit 62. The casing 60 is removably attached to the third portion 223 of the clip unit 22 of the mounting module 2, and includes an input port 601. The wireless transmitter 61 and the processing unit 62 are both disposed in the casing 60, and the wireless transmitter 61 is electrically connected to the processing unit 62. The processing unit 62 is electrically connected to the moisture detector 3 through the transmission wire 32 for receiving the notification signal outputted by the moisture detector 3, and is programmed to transmit the notification signal through the wireless transmitter 61. In this embodiment, the transmission wire 32 has a first end that is electrically connected to the connecting portion 31 of the moisture detector 3, and a second end that includes a connector 321 removably inserted into the input port 601 of the casing 60 so as to electrically connect the transmission wire 32 to the processing unit 62.

In this embodiment, the processing module 6 further includes an electricity detector 63 and a battery 64 that are disposed in the casing 60. The battery 64 is electrically connected to the moisture detector 3, the wireless transmitter 61, and the processing unit 62 to provide electricity thereto. The electricity detector 63 is electrically connected to the battery 64 to detect the residual capacity of the battery 64.

The camera device 9 is mounted to the mounting module 2 and includes a camera 90, two securing components 91, two connecting components 93 and a camera battery 905. In this embodiment, the securing components 91 of the camera device 9 are secured respectively to the two segments of the first portion 221 of the clip unit 22. Each of the connecting components 93 interconnects a respective one of the securing components 91 and the camera 90. The camera 90 includes a camera module 901, a camera transceiver 902, a camera processor 903 and a light-emitting diode (LED) light 904, and the camera battery 905 provides electricity to the components of the camera 90. The camera module 901 faces the sampling elements 52 for capturing an image of the sampling elements 52, and includes at least one lens, a shutter, an image sensing element, etc. The LED light 904 faces the sampling elements 52, is electrically connected to the camera processor 903, and is controlled by the camera processor 903 to emit light as the camera module 901 captures an image of the sampling elements 52. The camera processor 903 is electrically connected to the camera module 901 and the camera transceiver 902, and is configured to process the image captured by and received from the camera module 901 and to wirelessly transmit the image through the camera transceiver 902.

The user device 4 includes a device transceiver 41, a device processor 42, a notifying module 43, a power source 45, a memory 48 and a display 47. In this embodiment, the user device 4 is a mobile device, such as a smartphone, a cellular phone, a tablet, a personal digital assistant PDA and a smartwatch. The device transceiver 41 is configured to communicate wirelessly with the wireless transmitter 61 of the processing module 6 and the camera transceiver 902 of the camera 90 for receiving the notification signal and the image respectively therefrom. The device processor 42 is electrically connected to the device transceiver 41, the notifying module 43, the display 47 and the memory 48. The notifying module 43 is configured to output a wetness notification as controlled by the device processor 42 in response to receipt of the notification signal from the processing module 6 through the device transceiver 41. In one embodiment, the notifying module 43 can be implemented by a light emitting element 431 that emits light as the wetness notification, and/or a speaker 432 that outputs sound as the wetness notification. The memory 48 stores an application program (APP) 481 to be executed by the device processor 42 for executing various functions, such as wetness notification, urinalysis, etc. When the notifying module 43 is controlled by the device processor 42 to output the wetness notification, a caregiver who holds the user device 4 can thus be notified that the clothing article 10 is wet and has to be replaced. The power source 45 provides electricity to the device transceiver 41, the device processor 42, the notifying module 43, the memory 48 and the display 47. For example, the power source 45 may be a rechargeable battery.

Additionally, the device processor 42 is configured to start measuring a first predetermined time duration (e.g., 30 seconds) upon receiving the notification signal from the device transceiver 41, to output a control signal to the camera 90 through the device transceiver 41 after the first predetermined time duration has elapsed. In response to receipt of the control signal through the camera transceiver 902, the camera processor 903 enables the camera module 901 to capture a first image of the sampling elements 52, and transmits the first image to the user device 4 through the camera transceiver 902. The device processor 42 is further configured to control the display 47 to display the first image in response to receipt of the first image from the camera 90 through the device transceiver 41. The device processor 42 is further configured to start measuring a second predetermined time duration (e.g., 30 seconds) after the first predetermined time duration has elapsed and the first image is received, and to output the control signal to the camera 90 after the second predetermined time duration has elapsed. Similarly, the camera processor 903 enables the camera module 901 to capture a second image of the sampling elements 52 and transmits the second image to the user device 4 through the camera transceiver 902 in response to receipt of the control signal, and the device processor 42 controls the display 47 to display the second image in response to receipt of the second image from the camera 90 through the device transceiver 41. Similarly, the device processor 42 is further configured to start measuring a third predetermined time duration (e.g., 30 seconds) after the second predetermined time duration has elapsed and the second image is received, to output the control signal to the camera processor 903 to enable the camera module 901 to capture a third image of the sampling elements 52 after the third predetermined time duration has elapsed, and to control the display 47 to display the third image in response to receipt of the third image from the camera 90 through the device transceiver 41. Note that the camera module 901 may capture more than three images in other embodiments and the present disclosure is not limited in this respect. Each of the first predetermined time duration, the second predetermined time duration and the third predetermined time duration can be adjusted by using the APP 481 as required.

By this way, the caregiver can easily check the images captured by the camera 90 and displayed on the display 47 even if the caregiver is away from the wearer who is wearing the clothing article 10. The caregiver can observe the color(s) of the sampling elements 52 in the images displayed on the display 47, and compare the color(s) with a color chart so as to monitor physical condition of the wearer of the clothing article 10 in real time. In some embodiments, the device processor 42 may automatically, by executing the APP 481, analyze the color(s) of the sampling elements 52 in the images, determine the physical condition of the wearer based on analysis result, and control the display 47 to display the physical condition of the wearer thus determined.

In some embodiments, the device processor 42 may store the images captured by and received from the camera 90 in the memory 48, and the caregiver can manage and view the images stored in the memory 48 by using the APP 481. Further, the first image, the second image and the third image can also be transmitted to a computer (not shown) and stored therein for further processing to facilitate early diagnosis of certain diseases.

To sum up, in the present disclosure, by virtue of the moisture detector 3 that detects the surrounding moisture level and that makes the notifying module 43 of the user device 4 output the wetness notification when the surrounding moisture level is greater than the threshold moisture level, the caregiver can become aware that the clothing article 10 is wet even if the caregiver is away from the wearer who is wearing the clothing article 10. Further, the camera device 9 is controlled to capture the images of the sampling elements 52 at different time points (e.g., after the first, second and third time durations have respectively elapsed in sequence) upon the clothing article 10 becoming wet and to transmit the images to the user device 4, so that the caregiver can compare the color(s) of the sampling elements 52 in the images displayed on the display 47 with the color chart so as to monitor the physical condition of the wearer in real time.

In the description above, for the purposes of explanation, numerous specific details have been set forth in order to provide a thorough understanding of the embodiment (s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the present disclosure has been described in connection with what is considered the exemplary embodiment, it is understood that this disclosure is not limited to the disclosed embodiment but is intended to cover various arrangements included within the spirit and scope of the broadest interpretations and equivalent arrangements.

What is claimed is:

1. A wetness notification system for detecting and notifying wetness in a clothing article (10) that is configured for absorbing liquid, the wetness notification system comprising:
    a mounting module (2) configured to be mounted to the clothing article (10) and defining an accommodating space (295);
    a sampling unit (5) that extends into said accommodating space (295), and that includes a substrate (51) made of a flexible material and removably inserted into said accommodating space (295) of said mounting module (2), and at least one sampling element (52) disposed on said substrate (51) for contacting and sampling liquid within a space surrounded by the clothing article (10) for analysis;
    a moisture detector (3) mounted in said accommodating space (295), positioned between said mounting module (2) and said sampling unit (5), and configured to output a notification signal when a surrounding moisture level detected thereby is greater than a threshold moisture level, said sampling element (52) being disposed on a surface of said substrate (51) that faces away from said moisture detector (3);
    a processing module (6) including
        a casing (60) mounted to said mounting module (2),
        a wireless transmitter (61) disposed in said casing (60), and
        a processing unit (62) disposed in said casing (60), electrically connected to said moisture detector (3) and said wireless transmitter (61), and configured to receive the notification signal outputted by said moisture detector (3) and to transmit the notification signal through said wireless transmitter (61);
    a camera device (9) mounted to said mounting module (2) and including
        a camera (90) that includes a camera module (901) facing said sampling element (52) for capturing an image of said sampling element (52), a camera transceiver (902), and a camera processor (903) electrically connected to said camera module (901) and said camera transceiver (902) and configured to process the image captured by and received from said camera module (901) and to wirelessly transmit the image through said camera transceiver (902),
        at least one securing component (91) secured to said mounting module (2), and
        at least one connecting component (93) interconnecting said securing component (91) and said camera (90); and
    a user device (4) including
        a device transceiver (41) configured to communicate wirelessly with said wireless transmitter (61) and said camera transceiver (902) for receiving the notification signal and the image respectively therefrom,
        a display (47), and
        a device processor (42) electrically connected to said device transceiver (41) and said display (47), and configured to start measuring a first predetermined time duration upon receiving the notification signal from said device transceiver (41), to output a control signal to said camera processor (903) through said device transceiver (41) after the first predetermined time duration has elapsed to enable said camera module (901) to capture a first image of said sampling element (52), and to control said display (47) to display the first image in response to receipt of the first image from said camera (90) through said device transceiver (41).

2. The wetness notification system as claimed in claim 1, wherein said sampling unit (5) includes a plurality of sampling elements (52) disposed on said substrate (51) and spaced apart from one another.

3. The wetness notification system as claimed in claim 1, wherein said mounting module (2) includes a sleeve body (21), and a mounting seat (29) that is combined with said sleeve body (21) and that includes:
    a base plate (291) connected to said sleeve body (21); and
    a positioning wall (292) surrounding a periphery of said base plate (291), cooperating with said base plate (291) to define said accommodating space (295) where said moisture detector (3) is tightly disposed, and being formed with at least one notch (294) that is depressed toward said base plate (291),
    wherein said moisture detector (3) includes a connecting portion (31) extending through said notch (294), and a transmission wire (32) electrically connected between said connecting portion (31) and said processing module (6).

4. The wetness notification system as claimed in claim 3, wherein said positioning wall (292) is further formed with a through hole (293), and said substrate (51) includes a first segment (511) that is disposed in said accommodating space (295) and that cooperates with said base plate (291) to sandwich said moisture detector (3) therebetween, and a second segment (512) that extends from said first segment (511) through said through hole (293).

5. The wetness notification system as claimed in claim 3, wherein said mounting module (2) further includes a clip unit (22) including a first portion (221) removably and partially inserted into said sleeve body (21), a second portion (222) curvedly extending from said first portion (221), and a third portion (223) extending from said second portion (32),
    wherein said securing component (91) is secured to said first portion (221).

6. The wetness notification system as claimed in claim 4, wherein said casing (60) is removably attached to said third portion (223) of said clip unit (22).

7. The wetness notification system as claimed in claim 4, wherein said third portion (223) of said clip unit (22) is configured to cooperate with said first portion (221) to clip said mounting module (2) onto the clothing article (10) in a manner that said sleeve body (21) and said mounting seat

(29) are disposed at an inner side of the clothing article (10) and that said third portion (223) is disposed at an outer side of the clothing article (10) opposite to the inner side.

8. The wetness notification system as claimed in claim 1, wherein said camera (90) further includes a light-emitting diode (LED) light (904) facing said sampling element (52), electrically connected to said camera processor (903), and controlled by said camera processor (903) to emit light as said camera module (901) captures an image of said sampling element (52).

9. The wetness notification system as claimed in claim 1, wherein said user device (4) further includes a notifying module (43) electrically connected to said device processor (42) and configured to output a wetness notification as controlled by said device processor (42) in response to receipt of the notification signal.

10. The wetness notification system as claimed in claim 1, wherein said user device (4) is a mobile device.

11. The wetness notification system as claimed in claim 1, wherein said user device (4) is one of a smartphone, a cellular phone, a tablet, a personal digital assistant (PDA) and a smartwatch.

12. The wetness notification system as claimed in claim 1, wherein said device processor (42) is further configured to start measuring a second predetermined time duration after the first predetermined time duration has elapsed and the first image is received, to output the control signal to said camera processor (903) to enable said camera module (901) to capture a second image of said sampling element (52) after the second predetermined time duration has elapsed, and to control said display (47) to display the second image in response to receipt of the second image from said camera (90) through said device transceiver (41).

13. The wetness notification system as claimed in claim 11, wherein said device processor (42) is further configured to start measuring a third predetermined time duration after the second predetermined time duration has elapsed and the second image is received, to output the control signal to said camera processor (903) to enable said camera module (901) to capture a third image of said sampling element (52) after the third predetermined time duration has elapsed, and to control said display (47) to display the third image in response to receipt of the third image from said camera (90) through said device transceiver (41).

14. The wetness notification system as claimed in claim 12, wherein each of the first predetermined time duration, the second predetermined time duration and the third predetermined time duration is thirty seconds.

* * * * *